United States Patent
Shimoyama et al.

(10) Patent No.: US 11,617,494 B2
(45) Date of Patent: Apr. 4, 2023

(54) ENDOSCOPE SYSTEM, PROCESSOR, CALIBRATION APPARATUS, AND ENDOSCOPE

(71) Applicant: OLYMPUS CORPORATION, Hachioji (JP)

(72) Inventors: Masanori Shimoyama, Hino (JP); Rintaro Nishihara, Tokyo (JP); Sho Nakamura, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 584 days.

(21) Appl. No.: 16/780,774

(22) Filed: Feb. 3, 2020

(65) Prior Publication Data
US 2020/0268233 A1 Aug. 27, 2020

(30) Foreign Application Priority Data

Feb. 27, 2019 (JP) .............................. JP2019-034760

(51) Int. Cl.
*A61B 1/00* (2006.01)
(52) U.S. Cl.
CPC ........ *A61B 1/00057* (2013.01); *A61B 1/0002* (2013.01); *A61B 1/00004* (2013.01); *A61B 1/00158* (2013.01); *A61B 2562/0223* (2013.01)
(58) Field of Classification Search
CPC ............ A61B 1/00057; A61B 1/00004; A61B 1/0002; A61B 1/00158; A61B 2562/0223; A61B 1/00188; A61B 1/00006; G02B 7/282; G02B 23/2438; G02B 23/2476
See application file for complete search history.

(56) References Cited

U.S. PATENT DOCUMENTS

| 9,742,257 | B2 | 8/2017 | Shimoyama | |
|---|---|---|---|---|
| 9,769,384 | B2 | 9/2017 | Nishihara | |
| 10,165,184 | B2 | 12/2018 | Nishihara | |
| 10,379,373 | B2 | 8/2019 | Nishihara | |
| 2012/0162402 | A1* | 6/2012 | Amano | ............. A61B 1/00188 348/E7.085 |

(Continued)

FOREIGN PATENT DOCUMENTS

JP 2008096213 A 4/2008

OTHER PUBLICATIONS

U.S. Appl. No. 16/688,652; First Named Inventor: Masanori Shimoyama; Title: "Endoscope System, Processor and Endoscope", filed Nov. 19, 2019.

(Continued)

*Primary Examiner* — Timothy J Neal
*Assistant Examiner* — Sung Ham
(74) *Attorney, Agent, or Firm* — Holtz, Holtz & Volek PC

(57) ABSTRACT

An endoscope system includes an endoscope having a position/angle sensor and an amplifying circuit, a memory configured to store output error sensitivity data and a first wiring resistance value, and a processor including a signal processing circuit configured to process an output signal from the amplifying circuit. The signal processing circuit corrects an error of the output signal based on a value obtained by multiplying a difference between the first wiring resistance value and a processor wiring resistance value by the output error sensitivity data.

17 Claims, 6 Drawing Sheets

(56) References Cited

U.S. PATENT DOCUMENTS

| | | | |
|---|---|---|---|
| 2013/0141557 A1* | 6/2013 | Kawata | A61B 1/045 348/65 |
| 2016/0037079 A1* | 2/2016 | Gocho | A61B 1/045 348/240.3 |
| 2016/0331211 A1* | 11/2016 | Fujisawa | A61B 1/00027 |
| 2019/0089920 A1* | 3/2019 | Nakamura | A61B 1/00029 |

OTHER PUBLICATIONS

U.S. Appl. No. 16/693,217; First Named Inventor: Rintaro Nishihara; Title: "Endoscope System, Processor, and Endoscope", filed Nov. 22, 2019.

* cited by examiner

| ENDOSCOPE MODEL INFORMATION | OFFSET VOLTAGE SENSITIVITY Δ | WIRING RESISTANCE VALUE $R_{PGND}$ |
| --- | --- | --- |
| MODEL 1 | Δ1 | $R_{P1GND}$ |
| MODEL 2 | Δ2 | $R_{P2GND}$ |
| MODEL 3 | Δ3 | $R_{P3GND}$ |
| . . . | . . . | . . . |

ENDOSCOPE SYSTEM, PROCESSOR, CALIBRATION APPARATUS, AND ENDOSCOPE

CROSS REFERENCE TO RELATED APPLICATION

This application claims benefit of Japanese Application No. 2019-34760 filed in Japan on Feb. 27, 2019, the entire contents of which are incorporated herein by this reference.

BACKGROUND OF THE INVENTION

1. Field of the Invention

The present invention relates to an endoscope system, a processor, a calibration apparatus, and an endoscope capable of detecting a position of a movable member included in an image pickup optical system of an endoscope.

2. Description of the Related Art

An endoscope system includes, for example, an endoscope for observing a subject, and a processor for controlling the endoscope. In the endoscope system like this, a configuration is proposed in which an image formation state (for example, a focus position, a zoom position, and an aperture diameter) of an image pickup optical system for observing a subject is made adjustable. More specifically, the configuration is such that movable members such as a movable lens and an optical aperture that are movable by an actuator are provided in the image pickup optical system.

In order to move a movable member to a target position or a target angle accurately, it is necessary to detect the position or the angle of the movable member. An example of such a sensor (position/angle sensor) for position/angle detection is a Hall element. A Hall element generates a potential difference (Hall voltage) corresponding to a magnitude of a magnetic flux density that is incident, and outputs the potential difference as a detection signal. In order to detect the position of a movable member with the Hall element, for example, a magnet can be integrally connected to the movable member, and the Hall element can be disposed at a fixed portion (alternatively, the Hall element may be integrally connected to the movable member, and the magnet may be disposed at the fixed portion).

Incidentally, it is known that the detection signal of a Hall element includes an offset voltage. The offset voltage does not depend on a change in magnetic flux density, and therefore when the detection signal including an offset voltage is directly used in position detection, an error occurs to a detected position. Consequently, more accurate position detection is performed by correcting the offset voltage.

For example, Japanese Patent Application Laid-Open Publication No. 2008-96213 describes an art of passing a current for offset detection to respective terminals of a Hall element to obtain electric characteristics of the Hall element (resistance values among the four terminals of the Hall element), by switching to a current source for offset detection from a current source for control by a switching circuit, and correcting the unbalanced voltage of the Hall element based on the obtained electric characteristics.

SUMMARY OF THE INVENTION

An endoscope system according to one aspect of the present invention includes an endoscope, a processor to which the endoscope is connectable, and a memory that is readable by the processor, wherein the endoscope includes an image pickup optical system configured to form a subject image, a movable member configured to adjust an image formation state of the image pickup optical system, a position/angle sensor configured to detect a position or an angle of the movable member, and output a detection signal, and an amplifying circuit configured to amplify the detection signal and output the detection signal as an output signal, the memory stores output error sensitivity data based on a ratio of a change amount of an offset voltage included in a voltage of the output signal to a change amount of a wiring resistance value of wiring for supplying an operation current to the position/angle sensor, and a first wiring resistance value of the wiring for supplying the operation current in a calibration apparatus that obtains the output error sensitivity data, the processor includes a constant current circuit configured to supply the operation current to the position/angle sensor, a signal processing circuit configured to process the output signal from the amplifying circuit, and a processor memory that stores a processor wiring resistance value of wiring for supplying the operation current, in the processor, and the signal processing circuit reads the output error sensitivity data and the first wiring resistance value from the memory when the endoscope and the processor are connected, and corrects an error of the output signal based on a value obtained by multiplying a difference between the first wiring resistance value and the processor wiring resistance value by the output error sensitivity data.

A processor according to one aspect of the present invention is capable of connecting to an endoscope including a position/angle sensor configured to detect a position or an angle of a movable member configured to adjust an image formation state of an image pickup optical system, and output a detection signal, and an amplifying circuit configured to amplify the detection signal and output the detection signal as an output signal, and capable of reading a memory configured to store output error sensitivity data based on a ratio of a change amount of an offset voltage included in a voltage of the output signal to a change amount of a wiring resistance value of wiring for supplying an operation current to the position/angle sensor, and a first wiring resistance value of wiring for supplying the operation current, in a calibration apparatus that obtains the output error sensitivity data, and the processor includes a constant current circuit configured to supply the operation current to the position/angle sensor, a signal processing circuit configured to process the output signal from the amplifying circuit, and a processor memory configured to store a processor wiring resistance value of the wiring for supplying the operation current in the processor, wherein the signal processing circuit reads the output error sensitivity data and the first wiring resistance value from the memory when the endoscope is connected, and corrects an error of the output signal, based on a value obtained by multiplying a difference between the first wiring resistance value and the processor wiring resistance value by the output error sensitivity data.

A calibration apparatus according to one aspect of the present invention is connectable to an endoscope including a position/angle sensor configured to detect a position or an angle of a movable member configured to adjust an image formation state of an image pickup optical system, and output a detection signal, an amplifying circuit configured to amplify the detection signal and output the detection signal as an output signal, and an endoscope memory, and includes a constant current circuit configured to supply an operation current to the position/angle sensor, a signal processing circuit configured to process the output signal from the amplifying circuit, a resistance switcher configured to switch wiring of a first wiring resistance value for supplying the operation current, and second wiring that is for supplying the operation current, and is of a second wiring resistance value different from the first wiring resistance value, in the calibration apparatus, and a calibration memory configured to store the first wiring resistance value and the second wiring resistance value, wherein when the endoscope and the calibration apparatus are connected, the resistance switcher switches to the wiring of the first wiring resistance value, the signal processing circuit acquires a first output signal from the amplifying circuit, the resistance switcher switches to the second wiring of the second wiring resistance value, the signal processing circuit acquires a second output signal from the amplifying circuit, the signal processing circuit obtains output error sensitivity data, based on a ratio of a value obtained by subtracting the first output signal from the second output signal to a value obtained by subtracting the first wiring resistance value from the second wiring resistance value, and the signal processing circuit causes the endoscope memory to store the output error sensitivity data and the first wiring resistance value.

An endoscope according to one aspect of the present invention is connectable to a processor, and includes an image pickup optical system configured to form a subject image, a movable member configured to adjust an image formation state of the image pickup optical system, a position/angle sensor configured to detect a position or an angle of the movable member, and output a detection signal, an amplifying circuit configured to amplify the detection signal and output the detection signal as an output signal, and an endoscope memory configured to store output error sensitivity data based on a ratio of a change amount of an offset voltage included in a voltage of the output signal to a change amount of a wiring resistance value of wiring for supplying an operation current to the position/angle sensor, and a first wiring resistance value of wiring for supplying the operation current in a calibration apparatus that obtains the output error sensitivity data, wherein when the endoscope and the processor are connected, the output error sensitivity data and the first wiring resistance value are transmitted to the processor from the endoscope memory to cause the processor to correct an error of the output signal.

DETAILED DESCRIPTION OF THE PREFERRED EMBODIMENT

Hereinafter, an embodiment of the present invention will be described with reference to the drawings.

Embodiment 1

Since an endoscope is required to have a thinner diameter and a lighter weight, a signal processing circuit that obtains a position/angle of a movable member from a detection signal of a position/angle sensor such as a Hall element is disposed at a side of a processor that is connected to the endoscope. In contrast with this, an image pickup optical system is disposed in a distal end portion of the endoscope, and the position/angle sensor is also disposed in the distal end portion of the endoscope. Accordingly, a detection signal of the position/angle sensor and a return signal of a power feeding signal to the position/angle sensor are transmitted in the elongated endoscope from the distal end portion of the endoscope, are further transmitted in a cable that is extended from a proximal end side of the endoscope, and further pass through wiring in the processor to reach the signal processing circuit in the processor and the ground. In this way, the wiring from the position/angle sensor to the signal processing circuit in the processor and the ground is relatively long, and therefore electric resistance of the wiring itself cannot be ignored. The wiring resistance like this affects a position/angle detection result by the position/angle sensor, and wiring resistance to the ground from the position/angle sensor, which relates to the return signal of the power feeding signal, particularly has an influence on the offset voltage. Therefore, if the position/angle is calculated based on the detection signal including the offset voltage in which no wiring resistance is taken into consideration, an error may occur to a calculation result.

Further, a combination of an endoscope and a processor is not only one, but there occur combinations in which a plurality of kinds of processors are connectable to a certain endoscope, and a plurality of endoscopes are connectable to a certain processor, for example. In this case, the value of wiring resistance changes according to the combination, so that unless correction corresponding to the value of the wiring resistance is performed, the position/angle which is detected becomes inaccurate.

Further, a magnitude of the influence of wiring resistance on an offset voltage also depends on a variation of an amplifier (for example, a differential amplifier) that amplifies an output of the position/angle sensor.

The present embodiment is made in consideration of the point like this.

Figure 1:
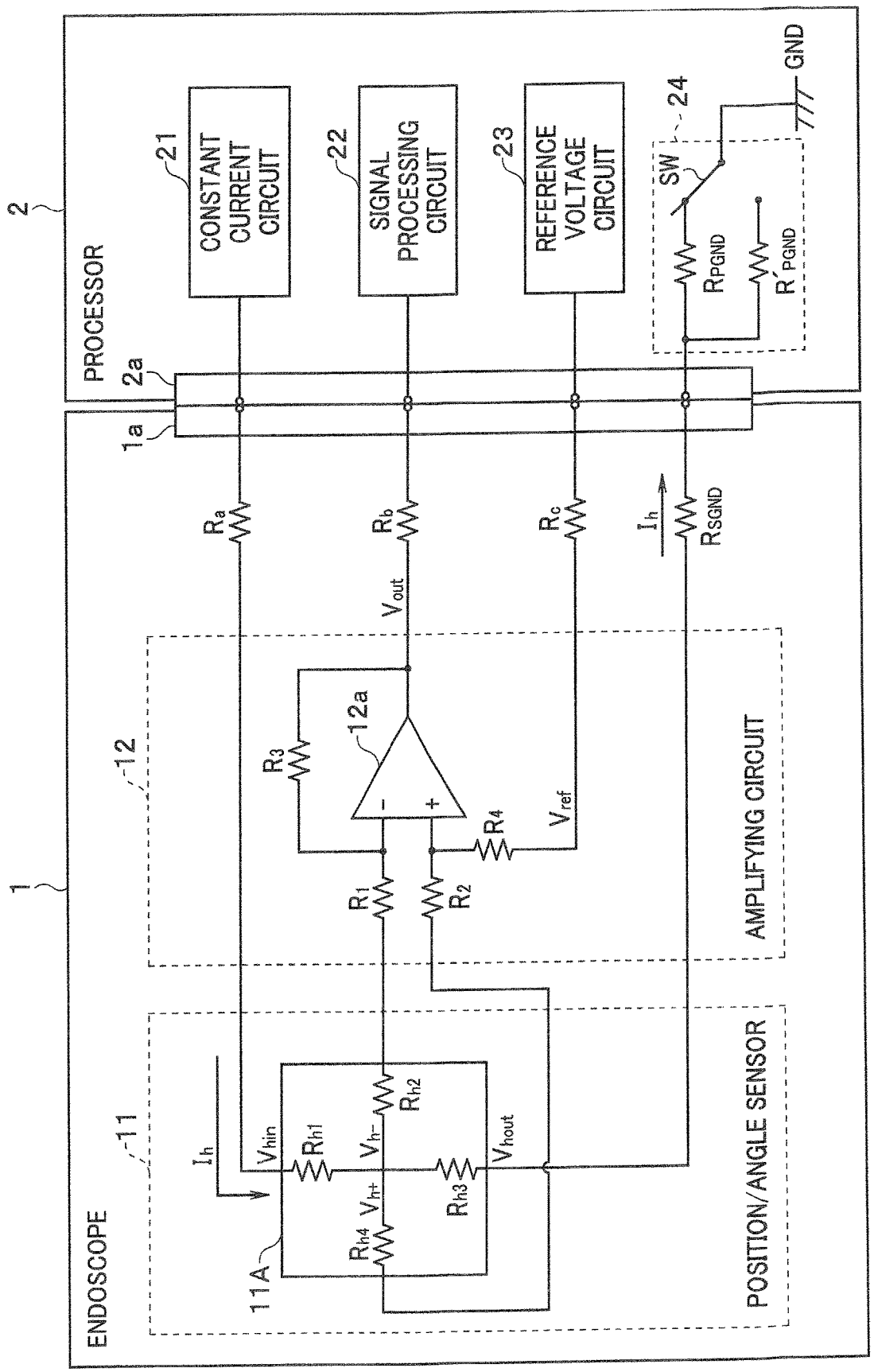
FIG. 1 is a diagram for explaining a principle that an offset voltage in an output voltage of a Hall element changes according to a resistance value of wiring in embodiment 1 of the present invention.

FIGS. 1 to 8 illustrate embodiment 1 of the present invention, and FIG. 1 is a diagram for explaining a principle that an offset voltage in an output voltage of a Hall element 11A changes in response to a resistance value of wiring.

An endoscope system illustrated in FIG. 1 includes an endoscope 1, and a processor 2 to which the endoscope 1 is connectable, and a connector 1a on an endoscope 1 side is connected to a connector receptacle 2a detachably and attachably on the processor 2 side.

FIG. 1 illustrates an example in which a calibration apparatus also serves as the processor 2. Here, the calibration apparatus is an apparatus for obtaining data (an offset voltage sensitivity Δ and a first wiring resistance value $R_{PGND}$ that are described later) for correcting an output signal (hereinafter, properly referred to as an output signal $V_{out}$) of a voltage $V_{out}$ that is obtained as a detection result. Note that the output signal $V_{out}$ is obtained as a result of a position or an angle of a movable member (a movable lens 14a illustrated in FIG. 4 that is described later, for example) by the endoscope 1.

Note that the calibration apparatus does not have to also serve as the processor 2, but may be an exclusive calibration apparatus that does not include such a function of performing signal processing of an image pickup signal as the ordinary processor 2 includes.

FIG. 1 illustrates an example in which a position/angle sensor 11 configured to detect a position or an angle of the movable member, and output a detection signal includes a Hall element 11A.

The Hall element 11A is a magnetic sensor configured to output a detection signal corresponding to a magnitude of a magnetic flux density which is incident on the magnetic sensor. In other words, when a magnetic field is applied in a perpendicular direction to a current direction, to a Hall drive current (constant current $I_h$) that is applied to the Hall element 11A, carriers (electrons, positive holes, and the like) receive Lorentz force in a perpendicular direction (referred to as $I_h \times B$ direction) to both a current direction ($I_h$ direction) and a magnetic field direction (B direction). Thereby, a difference occurs to a distribution density of carriers in both end surfaces in the $I_h \times B$ direction, of the Hall element 11A, and a voltage (Hall voltage) appears. By detecting a signal corresponding to the Hall voltage, the magnitude of the magnetic flux density which is incident on the Hall element 11A can be measured.

The endoscope 1 includes, for example, the position/angle sensor 11 including the Hall element 11A, and an amplifying circuit 12 configured to amplify a detection signal of the position/angle sensor 11 and output the detection signal as the output signal $V_{out}$. The processor 2 includes a constant current circuit 21 configured to supply an operation current to the position/angle sensor 11 (more specifically, the constant current $I_h$ to the Hall element 11A), a signal processing circuit 22 configured to process the output signal $V_{ow}$ from the amplifying circuit 12, a reference voltage circuit 23 configured to supply a signal of a reference voltage $V_{ref}$ to the amplifying circuit 12, and a resistance switcher 24 configured to switch wiring resistance in the processor 2, in a return path of the constant current $I_h$ from the position/angle sensor 11.

The constant current $I_h$ from the constant current circuit 21 is inputted to the Hall element 11A through a wiring resistance $R_a$. Here, a circuit configuration of the Hall element 11A is variously modelled, and therefore what is shown in FIG. 1 is only one modelling example of the Hall element 11A.

Note that hereinafter, concerning a certain resistance, a resistance itself and a resistance value of the resistance will be denoted by the same reference sign. Accordingly, for example, a resistance $R_a$ may be referred to, while a resistance value $R_a$ may also be referred to. Similarly, a current and a current value will be denoted by the same reference sign.

An input voltage to the Hall element 11A, of the constant current $I_h$ is set as $V_{hin}$, and an output voltage from the Hall element 11A is set as $V_{hout}$. Further, a resistance value on an input side, of the constant current $I_h$ in the Hall element 11A is set as $R_{h1}$, and a resistance value on an output side is set as $R_{h3}$. The constant current $I_h$ that is outputted from the Hall element 11A is connected to a ground GND through a wiring resistance $R_{SGND}$ in the endoscope 1, and, for example, a first wiring resistance $R_{PGND}$ in the processor 2.

The processor 2 is provided with the resistance switcher 24, so that wiring resistance in the processor 2 can be switched from the first wiring resistance $R_{PGND}$ (described as "$R_{PGND}$" here because of being the resistance R in the processor (P), which is connected to the ground GND) to a second wiring resistance $R'_{PGND}$ (prime "'" is added to "R" representing resistance here because of being a resistance in the same processor (P) different in resistance value from the first wiring resistance $R_{PGND}$) for calibration, or vice versa.

The switch SW of the resistance switcher 24 is preferably configured to be able to be switched electrically, and for example, a CMOS switch, a relay switch and the like can be used. Note that the switch SW of the resistance switcher 24 is not prevented from being a mechanical changeover switch. Switch of the resistance of the resistance switcher 24 is preferably automatic switch and reduces a burden on a user, but may be manual switch.

A voltage on one side in a Hall voltage that is generated in the Hall element 11A is set as $V_{h-}$, and a voltage on the other side is set as $V_{h+}$. A detection signal of the voltage $V_{h-}$ is connected to the amplifying circuit 12 through a resistance $R_{h2}$ in the Hall element 11A. Further, a detection signal of the voltage $V_{h+}$ is connected to the amplifying circuit 12 through a resistance $R_{h4}$ in the Hall element 11A.

The amplifying circuit 12 includes, for example, a differential amplifier 12a configured by an OP amplifier or the like, and a differential amplifying circuit 12A (see FIG. 4) including resistances $R_1$, $R_2$, $R_3$ and $R_4$.

The detection signal of the voltage $V_{h-}$ which is generated in the Hall element 11A passes through the resistance $R_1$ in the amplifying circuit 12 after passing through the resistance $R_{h2}$ in the aforementioned Hall element 11A, and is inputted to a negative input terminal of the differential amplifier 12a.

The detection signal of the voltage $V_{h+}$ which is generated in the Hall element 11A passes through the resistance $R_2$ in the amplifying circuit 12 after passing through the resistance $R_{h4}$ in the aforementioned Hall element 11A, and is inputted to a positive input terminal of the differential amplifier 12a.

The positive input terminal of the differential amplifier 12a is connected to the reference voltage circuit 23 through the resistance $R_4$ in the amplifying circuit 12 and the wiring resistance $R_c$. Here, a voltage (voltage between the resistance $R_4$ and the wiring resistance $R_c$) of the signal that is supplied to the amplifying circuit 12 from the reference voltage circuit 23 through the wiring resistance $R_c$ is the reference voltage $V_{ref}$.

The negative input terminal of the differential amplifier 12a is connected to an output terminal of the differential amplifier 12a through the resistance $R_3$.

The output terminal of the differential amplifier 12a is connected to the signal processing circuit 22 of the processor 2 through the wiring resistance $R_b$. Here, a voltage of a signal that is outputted from the output terminal of the amplifying circuit 12 is set as $V_{out}$.

According to the configuration like this, the amplifying circuit 12 configured as the differential amplifying circuit 12A is configured to differentially amplify the detection signal of the Hall voltage which is generated in the Hall element 11A.

The voltage $V_{out}$ of the signal which is outputted from the output terminal of the amplifying circuit 12 includes an offset voltage that does not depend on a change in the magnetic flux density which is incident on the Hall element 11A. A principle that the offset voltage changes in response to the wiring resistance value, and a method for acquiring data for correcting a change in the offset voltage corresponding to the wiring resistance value are described with reference to FIG. 1.

First, the output voltage $V_{out}$ from the amplifying circuit 12 is calculated from mathematical expression 1 as follows by using the voltages $V_{h+}$ and $V_{h-}$ that are generated in the Hall element 11A.

$$V_{out} = \frac{R_3}{R'_1}(V_{h+} - V_{h-}) + (1-k)V_{h+} + k \cdot V_{ref} \quad \text{[Mathematical expression 1]}$$

Here, k, $R'_1$, and $R'_2$ appearing in k are values that are collectively shown in mathematical expression 2 as follows.

$$\begin{cases} R'_1 = R_1 + R_{h2} \\ R'_2 = R_2 + R_{h4} \\ k = \frac{R'_2}{R'_1} \cdot \frac{R'_1 + R_3}{R'_2 + R_4} \end{cases} \quad \text{[Mathematical expression 2]}$$

Further, when $R_{h2}=R_{h4}$, and $R_{h1}=R_{h3}$ are established, the voltages $V_{h+}$ and $V_{h-}$ that are generated in the Hall element 11A are expressed as shown in mathematical expression 3 and mathematical expression 4 as follows, by using a detection sensitivity $\alpha$(mV/(mA·mT)) of the Hall element 11A, a magnetic flux density B (mT), the constant current $I_h$, the input voltage $V_{hin}$ of the constant current $I_h$ to the Hall element 11A, and the output voltage $V_{hout}$ of the constant current $I_h$ from the Hall element 11A.

$$V_{h+} = \frac{\alpha \cdot B \cdot I_h}{2} + \frac{V_{hin} + V_{hout}}{2} \quad \text{[Mathematical expression 3]}$$

$$V_{h-} = -\frac{\alpha \cdot B \cdot I_h}{2} + \frac{V_{hin} + V_{hout}}{2} \quad \text{[Mathematical expression 4]}$$

In the output voltage $V_{out}$ that is given as shown in mathematical expressions 1 to 4 described above, the offset voltage $V_{off}$ to which attention is paid in the present embodiment is as shown in mathematical expression 5 as follows (although there are other offset voltage parts (for example, $k \cdot V_{ref}$) that do not depend on the magnetic flux density B in the output voltage $V_{out}$, attention is paid to the offset voltage $V_{off}$ shown in mathematical expression 5 in the present embodiment).

$$V_{off} = (1-k) \cdot \frac{V_{hout}}{2} \quad \text{[Mathematical expression 5]}$$

The offset voltage $V_{off}$ depends on the output voltage $V_{hout}$ of the constant current $I_h$ from the Hall element 11A, whereas the $V_{hout}$ depends on a ground resistance value $R_{GND}$ (a value obtained by adding up the wiring resistance value $R_{SGND}$ on the endoscope 1 side, and the wiring resistance value $R_{PGND}$ on the processor 2 side) shown in mathematical expression 6, and is given as shown in mathematical expression 7.

$$R_{GND} = R_{SGND} + R_{PGND} \quad \text{[Mathematical expression 6]}$$

$$V_{hout}(R_{GND}) = V_{GND} + I_h \cdot R_{GND} = I_h \cdot R_{GND} \quad \text{[Mathematical expression 7]}$$

The ground level $V_{GND}$ is generally 0 (V), which is used in the second equality in mathematical expression 7.

When mathematical expression 7 is substituted into mathematical expression 5, mathematical expression 8 is yielded.

$$V_{off} = \frac{(1-k) \cdot I_h}{2} \cdot R_{GND} = \quad \text{[Mathematical expression 8]}$$
$$\frac{(1-k) \cdot I_h}{2} \cdot (R_{SGND} + R_{PGND})$$

As shown in mathematical expression 7, the voltage $V_{hout}$ is equal to the ground level $V_{GND}$ when $R_{GND}=0$ ($\Omega$) is established, but is higher than the ground level $V_{GND}$ by $I_h \cdot R_{GND}$ when $R_{GND} \approx 0$ ($\Omega$).

In the endoscope system, a wiring length to the ground GND of the processor 2 from the Hall element 11A that is disposed in the distal end portion of the endoscope 1 is relatively long, so that dealing $R_{GND}$ as $R_{GND} \approx 0$ ($\Omega$) is not suitable.

Further, $R_{GND}=R_{SGND}+R_{PGND}$ is established, so that when the ground resistance value $R_{GND}$ changes according to a combination of the endoscope 1 and the processor 2, the voltage $V_{hout}$ changes, and the offset voltage $V_{off}$ also changes by extension.

From a viewpoint as above, a method for acquiring data for properly correcting the offset voltage $V_{off}$, data for correcting the output voltage $V_{out}$ of the Hall element 11A which is amplified by the amplifying circuit 12 by extension, according to the combination of the endoscope 1 and the processor 2 is described.

Figure 2:
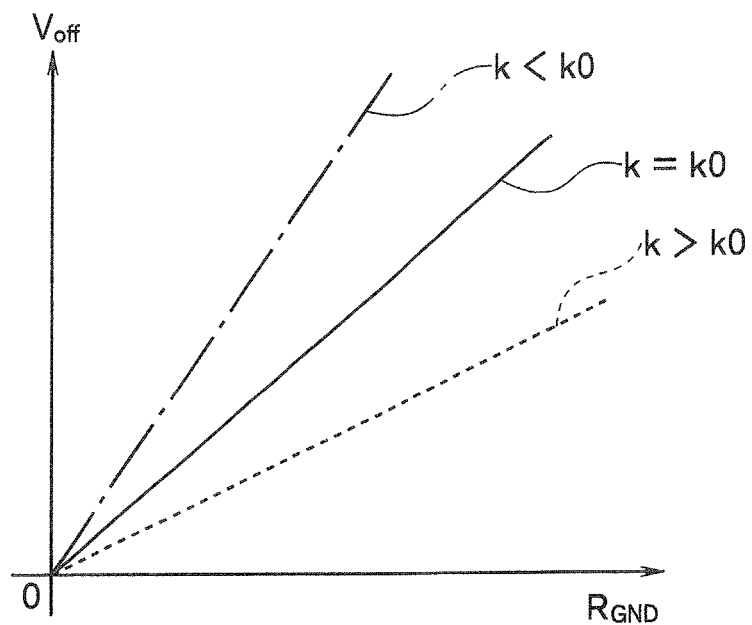
FIG. 2 is a diagram illustrating a relationship between a ground resistance value $R_{GND}$ and an offset voltage $V_{off}$ in embodiment 1 described above.

FIG. 2 is a diagram illustrating a relationship between the ground resistance value $R_{GND}$ and the offset voltage $V_{off}$.

The offset voltage $V_{off}$ increases proportionally to the ground resistance value $R_{GND}$ as shown in mathematical expression 8. Note that if the resistances $R_1$ to $R_4$ of the differential amplifier have variations (for example, variations for each of the individual endoscopes 1), the value of k also varies from the relationship as shown in mathematical expression 2. Thereby, when the value of (1-k) varies, a gradient of the change amount of the offset voltage $V_{off}$ to the change amount of the ground resistance value $R_{GND}$ differs for each of the individual endoscopes 1, for example.

More specifically, when k is smaller than a certain value k0 (k<k0), (1-k)>(1-k0) is established, so that the gradient of the change amount of the offset voltage $V_{off}$ to the change amount of the ground resistance value $R_{GND}$ is larger at a time of (k<k0) than at a time of (k=k0) (see a chain line in FIG. 2). When k is larger than the certain value k0 (k0<k), (1-k0)>(1-k) is established, so that the aforementioned gradient is smaller at a time of (k0<k) than at a time of (k=k0) (see a dotted line in FIG. 2).

Thus, the offset voltage sensitivity $\Delta$ is estimated for each of the individual endoscopes 1. Here, the offset voltage sensitivity $\Delta$ is output error sensitivity data showing a ratio of the change amount of the offset voltage $V_{off}$ included in the voltage $V_{out}$ of the output signal, to the change amount of the wiring resistance value of wiring for supplying an operation current to the position/angle sensor 11. Therefore, the output of the Hall element 11A is made constant first.

Figure 4:
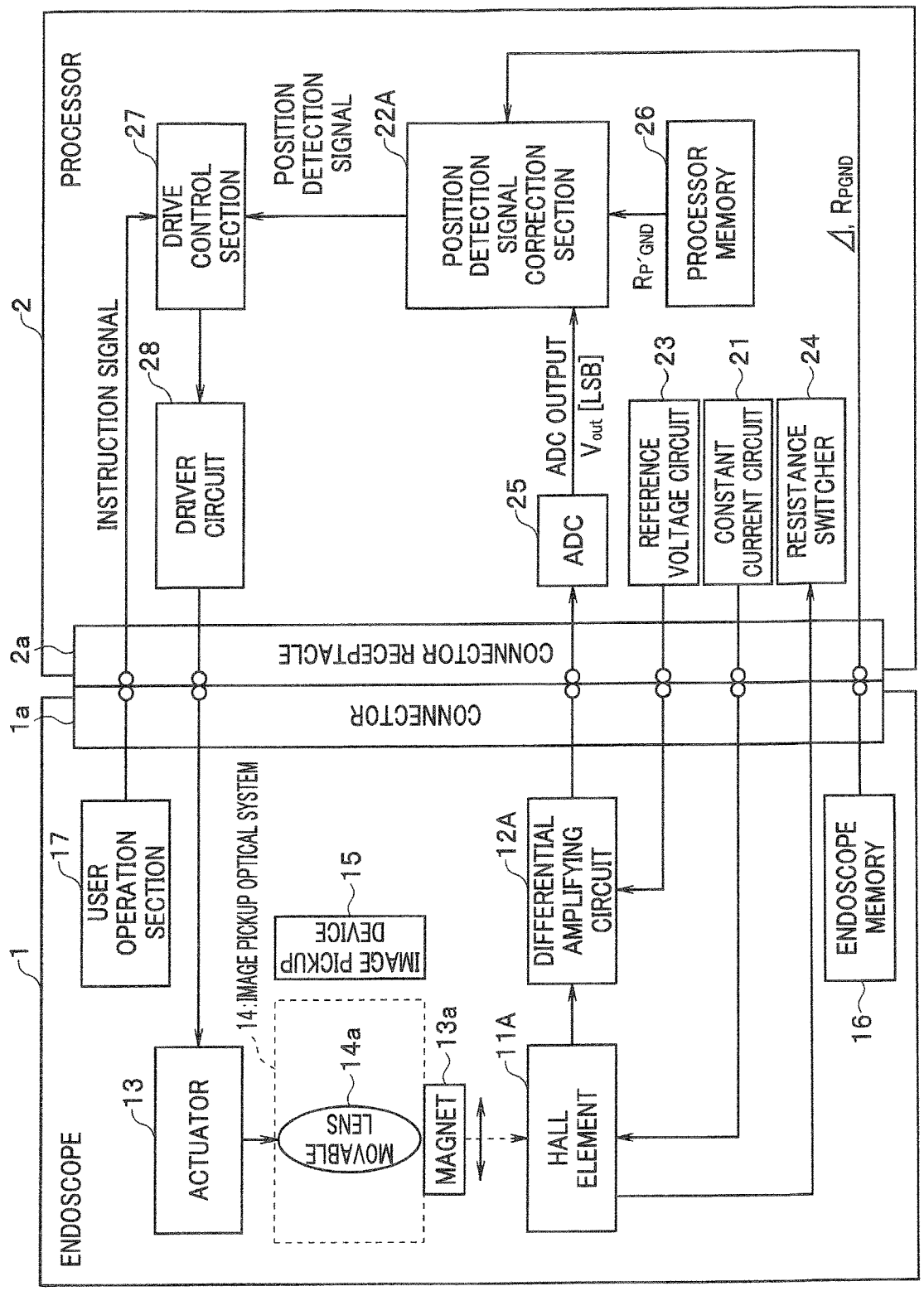
FIG. 4 is a block diagram illustrating a configuration example of an endoscope system in which an endoscope and a processor are connected detachably and attachably in embodiment 1 described above.

More specifically, the movable lens 14a is moved by passing a current to the actuator 13 from the driver circuit 28 of the processor 2 as illustrated in FIG. 4 which is described later, and a state where the movable lens 14a abuts on an end of a movable range (mechanical end portion) is kept. Thereby, a position of a magnet 13a to the Hall element 11A becomes constant, and the magnetic flux density B that is incident on the Hall element 11A is kept constant.

Note that in order to keep output of the Hall element 11A constant, a method that makes the magnetic flux density incident on the Hall element 11A zero (mT) (for example, a method that uses a magnetic shield, or performs measurement before attaching (or after removing) the magnet 13a) may be used, besides using the method for causing the movable lens 14a to abut on the end of the movable range.

In a state where the magnetic flux density B is kept constant, the wiring resistance in the processor 2 is switched to the first wiring resistance $R_{PGND}$ for detection by the resistance switcher 24, and the signal processing circuit 22 acquires the first output voltage $V_{out}$ ($R_{PGND}$) from the amplifying circuit 12. Further, in the state, the wiring resistance in the processor 2 is switched to the second wiring resistance $R'_{PGND}$ for calibration by the resistance switcher 24, and the signal processing circuit 22 acquires the second output voltage $V_{out}$ ($R'_{PGND}$) from the amplifying circuit 12.

Note that the wiring resistance $R_b$ is present between the amplifying circuit 12 and the signal processing circuit 22, but voltage reduction by the wiring resistance $R_b$ can be ignored by acquiring the output voltage $V_{out}$ with a very small current, or the wiring resistance $R_b$ is already known, and the current value from the amplifying circuit 12 is also acquired, whereby the signal processing circuit 22 can accurately calculate the output voltage $V_{out}$.

Under a condition that the magnetic flux density B is kept constant, a term dependent on the magnetic flux density B in the output voltage $V_{out}$ shown in mathematical expression 1 at a time of the wiring resistance being $R_{PGND}$, and the term dependent on the magnetic flux density B in the output voltage $V_{out}$ at a time of the wiring resistance being $R'_{PGND}$ are equal. Therefore, in a difference in the output voltage $\{V_{out}(R'_{PGND})-V_{out}(R_{PGND})\}$, a term dependent on the magnetic flux density B is cancelled, and a term (for example, $k \cdot V_{ref}$) that is not dependent on the wiring resistances $R_{PGND}$ and $R'_{PGND}$ in the processor 2 in the output voltage $V_{out}$ is also cancelled. As a result, the difference in the output voltage $\{V_{out}(R'_{PGND})-V_{out}(R_{PGND})\}$ becomes equal to a difference of the offset voltage $V_{off}$ $\{V_{off}(R'_{PGND})-V_{off}(R_{PGND})\}$, as shown in mathematical expression 9 as follows.

$$V_{off}(R'_{PGND})-V_{off}(R_{PGND})=\{V_{out}(R'_{PGND})-V_{out}(R_{PGND})\} \quad \text{[Mathematical expression 9]}$$

Figure 3:
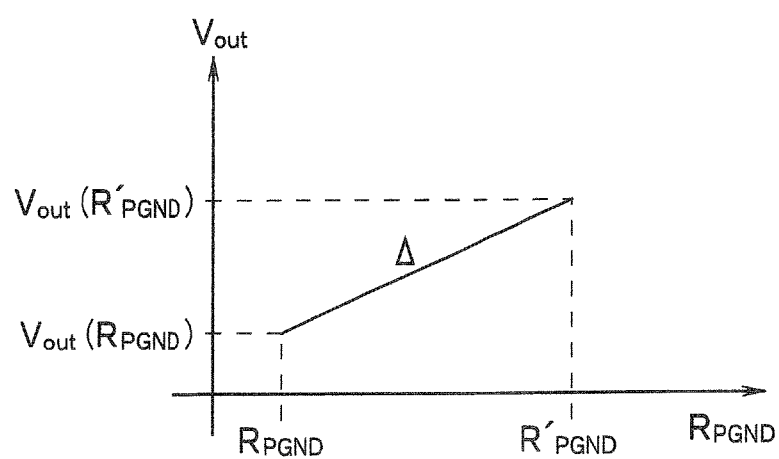
FIG. 3 is a diagram illustrating an example of an offset voltage sensitivity 4 in embodiment 1 described above.

Accordingly, the difference in the offset voltage $V_{off}$ can be obtained as the difference in the output voltage $V_{out}$. If the difference in the offset voltage $V_{off}$ which is obtained in this way is used, the offset voltage sensitivity Δ showing the change amount (that is, a gradient) of the offset voltage $V_{off}$ to the change amount of the wiring resistance value $R_{PGND}$ can be calculated as shown in mathematical expression 10 as follows. Here, FIG. 3 is a diagram illustrating an example of the offset voltage sensitivity Δ.

$$\Delta = \frac{V_{out}(R'_{PGND}) - V_{out}(R_{PGND})}{R'_{PGND} - R_{PGND}} = \frac{(1-k) \cdot I_h}{2} \quad \text{[Mathematical expression 10]}$$

The wiring resistances $R_{PGND}$ and $R'_{PGND}$ in the processor 2 are already known, by using the wiring resistances $R_{PGND}$ and $R'_{PGND}$ of resistance values with predetermined precision respectively, or by obtaining the resistance values by directly measuring the wiring resistances $R_{PGND}$ and $R'_{PGND}$, or by being estimated from the value of the constant current $I_h$ of the constant current circuit 21 and a measured voltage. The wiring resistance values $R_{PGND}$ and $R'_{PGND}$ are stored in advance in a processor memory 26 (see FIG. 4) that also serves as a calibration memory.

The offset voltage sensitivity Δ (output error sensitivity data) which is calculated in this way, and the wiring resistance value (may be either $R_{PGND}$ or $R'_{PGND}$, but in this case, $R_{PGND}$, for example) which is used in measurement are stored in a memory readable by the processor 2, in this case, an endoscope memory 16 (see FIG. 4), for example.

Next, a method for correcting the output voltage $V_{out}$ which is obtained by detecting a position or an angle by using the offset voltage sensitivity Δ and the wiring resistance value $R_{PGND}$ will be described.

A case of connecting the endoscope 1 to a second processor 2 that is different from the processor 2 which is the calibration apparatus that measures the offset voltage sensitivity Δ is considered. At this time, the wiring resistance value on the endoscope 1 side remains to be $R_{SGND}$, but the wiring resistance value on the processor 2 side changes from the wiring resistance value $R_{PGND}$ in the calibration apparatus to the processor wiring resistance value $R_{P'GND}$ (here, prime "'" is added to "P" indicating the processor 2, due to the resistance R in the second processor 2, which is connected to the ground GND).

The processor wiring resistance value $R_{P'GND}$ generally differs from the first wiring resistance value $R_{PGND}$ illustrated in FIG. 1 (further also differs from the second wiring resistance value $R'_{PGND}$), so that even when the movable lens 14a located in the same position is measured with the Hall element 11A, the output voltage $V_{out}$ of the endoscope 1 that is received by the second processor 2 is different from the output voltage $V_{out}$ that is received by the processor 2 which is the calibration apparatus, as illustrated in FIG. 3.

When the output voltage $V_{out}$ that is received by the processor 2 which is the calibration apparatus is set as a reference, a deviation of the output voltage $V_{out}$ which is received by the second processor 2 is what is obtained by multiplying the difference between the processor wiring resistance value $R_{P'GND}$ and the first wiring resistance value $R_{PGND}$ by the offset voltage sensitivity Δ. Accordingly, an output voltage $V_{correction}$ that is obtained by correcting the output voltage $V_{out}$ that is received by the second processor 2 to match the output voltage $V_{out}$ that is received by the calibration apparatus is calculated as shown in mathematical expression 11 as follows.

$$V_{correction} = V_{out} + \alpha \cdot (R_{PGND} - R_{P'GND}) \quad \text{[Mathematical expression 11]}$$

Next, a more specific configuration example of the endoscope system will be described with reference to FIG. 4. FIG. 4 is a block diagram illustrating a configuration example of the endoscope system in which the endoscope 1 and the processor 2 are connected detachably and attachably. Note that processing of an image pickup signal, supply of illuminating light and the like in the endoscope system are similar to processing of an image pickup signal, supply of illuminating light and the like in an ordinary endoscope, so that illustration and explanation of the processing of an image pickup signal, supply of illuminating light and the like in the endoscope system are omitted, and a configuration relating to position/angle detection of the movable members is mainly illustrated in FIG. 4 and explained.

First, in an endoscope memory 16 of the endoscope 1, the offset voltage sensitivity Δ obtained by a separate calibration apparatus and the first wiring resistance value $R_{PGND}$ are already stored. As an example of correcting the output voltage $V_{out}$ that is received by the second processor 2 by connecting the endoscope 1 like this to the second processor 2 which is different from the calibration apparatus that obtains the offset voltage sensitivity Δ will be described with reference to FIG. 4.

Note that in the example, the second processor 2 illustrated in FIG. 4 also includes the function of the calibration apparatus as shown in the processor 2 in FIG. 1. However, for the purpose of only correcting the output voltage $V_{out}$, the second processor 2 which does not include the function of the calibration apparatus may be adopted (in this case, the resistance switcher 24 does not have to be included).

The endoscope system illustrated in FIG. 4 is configured in such a manner that the endoscope 1 and the processor 2 (the aforementioned second processor 2) which is configured separately from the endoscope 1 are connected by the connector 1a and the connector receptacle 2a detachably and attachably.

The endoscope 1 includes the aforementioned Hall element 11A, and the differential amplifying circuit 12A as the specific example of the amplifying circuit 12, and includes the actuator 13, an image pickup optical system 14, an image pickup device 15, the endoscope memory 16, and a user operation section 17.

The image pickup optical system 14 forms an optical image of a subject (a subject image) on an image pickup surface of the image pickup device 15. The image pickup optical system 14 includes the movable lens 14a, and the movable lens 14a is an optical element movable in a direction of an optical axis of the image pickup optical system 14. When the movable lens 14a moves in the direction of the optical axis, an image formation state of the image pickup optical system 14 is adjusted, and, for example, a focus position (or a zoom position) is changed. Accordingly, the movable lens 14a functions as, for example, a focus lens (or a zoom lens). Note that the movable lens 14a is cited as an example of the movable member that adjusts the image formation state of the image pickup optical system 14 here, but the movable member is not limited to the lens, but may be other optical elements such as an optical filter, an optical aperture, a prism, and a mirror.

The image pickup device 15 has a plurality of pixels arranged on the image pickup surface, and generates an image pickup signal configured by a plurality of pixel signals by photoelectrically converting a subject image formed by the image pickup optical system 14 in the respective pixels. Note that an image pickup system is configured by including the image pickup optical system 14 and the image pickup device 15. Here, an example in which the endoscope system is an electronic endoscope system is described. However, the endoscope system is not limited to the electronic endoscope system, but may be an optical endoscope system capable of adjusting the image formation state of the image pickup optical system 14. Further, the endoscope system may be for medical use, industrial use, and other uses such as an academic use.

The actuator 13 moves the movable lens 14a in the optical axis direction, has a coil and a magnet, for example, and is configured as a voice coil motor (VCM: voice coil motor) that generates a drive force by an electromagnetic force (but is not limited to a voice coil motor).

Further, the magnet 13a is configured by a permanent magnet or the like, and is connected to the movable lens 14a, which is the movable member, to move in the optical axis direction integrally with the movable lens 14a. A magnetic field generated by the magnet 13a is used for detecting a position (or an angle of the movable member (for example, the optical aperture) as described above, but explanation will be made by mainly citing the position as an example hereinafter) of the movable lens 14a which moves integrally with the magnet 13a. Here, when the voice coil motor is used as the actuator 13, for example, the magnet 13a can be used as a part of the voice coil motor (from the viewpoint of achieving reduction in size of an endoscope distal end portion, this configuration can be adopted).

More specifically, the magnet 13a is fixed to a movable portion such as a movable barrel that holds the movable lens 14a, for example, and a coil of the actuator 13 is attached to a fixed portion such as a fixed barrel that holds the movable barrel movably in the optical axis direction. By applying a current to the coil located in the magnetic field generated by the magnet 13a, a Lorentz force occurs to the coil, and since the fixed barrel is fixed, the movable portion moves in the optical axis direction by a counteraction of the Lorentz force.

Note that a moving magnet type voice coil motor is described here, but a moving coil type voice coil motor may be adopted.

The Hall element 11A is disposed by being fixed to a fixed portion side to face the magnet 13a, and is a position/angle sensor configured to detect a position in the optical axis direction of the movable lens 14a and output a detection signal.

The differential amplifying circuit 12A amplifies an analogue detection signal that is outputted from the Hall element 11A. Note that as the amplifying circuit 12, the differential amplifying circuit 12A is cited as an example here, but the amplifying circuit 12 is not limited to the differential amplifying circuit 12A.

The endoscope memory 16 is a nonvolatile writable memory circuit (endoscope memory circuit). In the endoscope memory 16 of the endoscope 1 which is connected to the calibration apparatus and is subjected to calibration, the offset voltage sensitivity Δ that is output error sensitivity data, and the first wiring resistance value $R_{PGND}$ of wiring for supplying an operation current in the calibration apparatus that obtains the offset voltage sensitivity Δ are stored as described above.

Further, in the endoscope memory 16, endoscope model information (model number, serial number and the like) relating to the endoscope 1, other various kinds of information relating to the endoscope 1 and the like are stored.

The user operation section 17 is an operation device (user operation device) for adjusting the image formation state (the focus position, the zoom position and the like) of the image pickup optical system 14 as described above. In other words, the user operates the user operation section 17, and thereby an instruction signal indicating a target position of the movable lens 14a is transmitted to the processor 2 side from the user operation section 17. Citing an example, whether the target position of the movable lens 14a is made a far point focus position or a near point focus position is set by the user operation section 17 (it goes without saying that the focus position is not limited to the two-point focus of the far point and the near point, but the focus position (or the zoom position) may be changed continuously).

Note that in this case, manual focus by setting from the user operation section 17 is described. However, focus is not limited to manual focus, but autofocus or the like based on an image pickup signal obtained from the image pickup device 15 may be performed. Note that the user operation section 17 is also used when an operation relating to image pickup, and other operations to the endoscope system are performed, but explanation is omitted here.

As described above, the connector 1a of the endoscope 1 is detachably and attachably connected to the connector receptacle 2a of the processor 2 mechanically and electrically. When the endoscope 1 and the processor 2 are connected, signals that are transmitted and received through the connector 1a and the connector receptacle 2a are as follows, for example.

The endoscope 1 receives from the processor 2 a drive signal to the actuator 13, a signal of the reference voltage $V_{ref}$ to the differential amplifying circuit 12A, and a signal of the constant current $I_h$ to the Hall element 11A. Further, the endoscope 1 transmits to the processor 2 an instruction signal from the user operation section 17, the output signal $V_{out}$ from the differential amplifying circuit 12A, a return signal of the constant current $I_h$ from the Hall element 11A, and the data of the endoscope memory 16.

The processor 2 acquires an image pickup signal from the endoscope 1, performs signal processing to generate a video signal, and outputs the video signal to a monitor or the like to cause the monitor or the like to display an endoscope image.

The processor 2 includes the constant current circuit 21, a position detection signal correction section 22A, the reference voltage circuit 23, the resistance switcher 24, an ADC 25, a processor memory 26, a drive control section 27, and a driver circuit 28, as components relating to drive of the image pickup optical system 14.

The driver circuit 28 outputs a drive signal to the actuator 13, and drives the actuator 13, based on control of the drive control section 27. More specifically, the driver circuit 28 applies a drive signal of a predetermined current value to the coil of the actuator 13, and thereby the movable portion including the movable lens 14a and the magnet 13a is moved by an electromagnetic force.

The ADC 25 is an analogue/digital converter (A/D converter) configured to convert the analogue output signal $V_{out}$ that is outputted from the Hall element 11A and is amplified by the differential amplifying circuit 12A into a digital signal $V_{out}$ (LSB).

The constant current circuit 21 supplies a current of the constant current value $I_h$ (a bias current to the Hall element 11A) to the Hall element 11A.

The reference voltage circuit 23 supplies a signal of the reference voltage $V_{ref}$ to the differential amplifying circuit 12A.

The resistance switcher 24 is provided when the processor 2 includes the function of the calibration apparatus configured to measure the offset voltage sensitivity Δ, and switches the wiring of the first wiring resistance $R_{PGND}$ in the processor 2 and the second wiring of the second wiring resistance value $R'_{PGND}$ that is different from the first wiring resistance value $R_{PGND}$, as illustrated in FIG. 1.

The processor memory 26 is a nonvolatile writable memory circuit (processor memory circuit). In the processor memory 26, the processor wiring resistance value $R_{PGND}$ which is used when the position/angle of the movable lens 14a is detected is stored.

Further, when the processor 2 includes the function of the calibration apparatus and includes the resistance switcher 24, the second wiring resistance value $R'_{PGND}$ is also stored in the processor memory 26 which also serves as a calibration memory. At this time, the constant current circuit 21 also serves as a second constant current circuit, and the signal processing circuit 22 also serves as a second signal processing circuit.

In the processor memory 26, processor model information (model number, serial number and the like) relating to the processor 2, a processing program that is executed in the processor 2, various parameters that are used in the processor 2, a set value that is set to the endoscope system by the user, other various kinds of information relating to the processor 2 and the like are stored.

The position detection signal correction section 22A is a circuit (position detection signal correction circuit) corresponding to the signal processing circuit 22 illustrated in FIG. 1, and receives a signal of the output voltage $V_{out}$ from the amplifying circuit 12 of the endoscope 1. Further, the position detection signal correction section 22A receives the offset voltage sensitivity Δ and the first wiring resistance value $R_{PGND}$ (the first wiring resistance value in the calibration apparatus which measures the offset voltage sensitivity Δ) from the endoscope memory 16, and receives the processor wiring resistance value $R_{PGND}$ relating to the processor 2 from the processor memory 26.

The position detection signal correction section 22A performs an arithmetic operation as shown in mathematical expression 11 based on the respective input values, and thereby calculates the corrected output voltage $V_{correction}$. Thereafter, the position detection signal correction section 22A generates a position detection signal when a detection target is the position based on the output voltage $V_{correction}$, and outputs the position detection signal to the drive control section 27.

Note that here, assuming the case where position detection is performed, the name "position detection signal correction section (position detection signal correction circuit)" is used, but when angle detection is performed, a name "angle detection signal correction section (angle detection signal correction circuit)" may be used, and when a position and an angle are detected as desired, a name such as "position/angle detection signal correction section (position/angle detection signal correction circuit)" can be used.

The drive control section 27 is a control circuit (drive control circuit) configured by including an arithmetic operation processing circuit such as a CPU, and configured to control the driver circuit 28 so that a position of the movable lens 14a indicated by the position detection signal from the position detection signal correction section 22A corresponds to a target position indicated by an instruction signal from the user operation section 17.

More specifically, the drive control section 27 outputs a control signal to the driver circuit 28 and performs feedback control so that a current having such a current value that a difference between a present position of the movable lens 14a indicated by the detection signal and the target position of the movable lens 14a indicated by the instruction signal from the user operation section 17 becomes zero (in other words, the position of the movable lens 14a becomes the target position) is outputted from the driver circuit 28.

When the processor 2 including the function of the calibration apparatus as illustrated in FIG. 4 is set at a calibration mode manually or automatically, the processor 2 measures the offset voltage sensitivity Δ as described with reference to FIG. 1 to FIG. 3, and performs processing of causing the endoscope memory 16 to store the measured offset voltage sensitivity Δ and the processor wiring resistance value $R_{PGND}$ that doubles as the first wiring resistance value. Here, the processor 2 is automatically set at the calibration mode when the offset voltage sensitivity Δ and the first wiring resistance value $R_{PGND}$ are not stored in the endoscope memory 16 of the endoscope 1 connected to the processor 2, for example. Manual setting of the calibration mode is performed by an operation of the user operation section 17 or an operation of a processor operation section (processor operation device) not illustrated which is provided in the processor 2.

Figure 5:
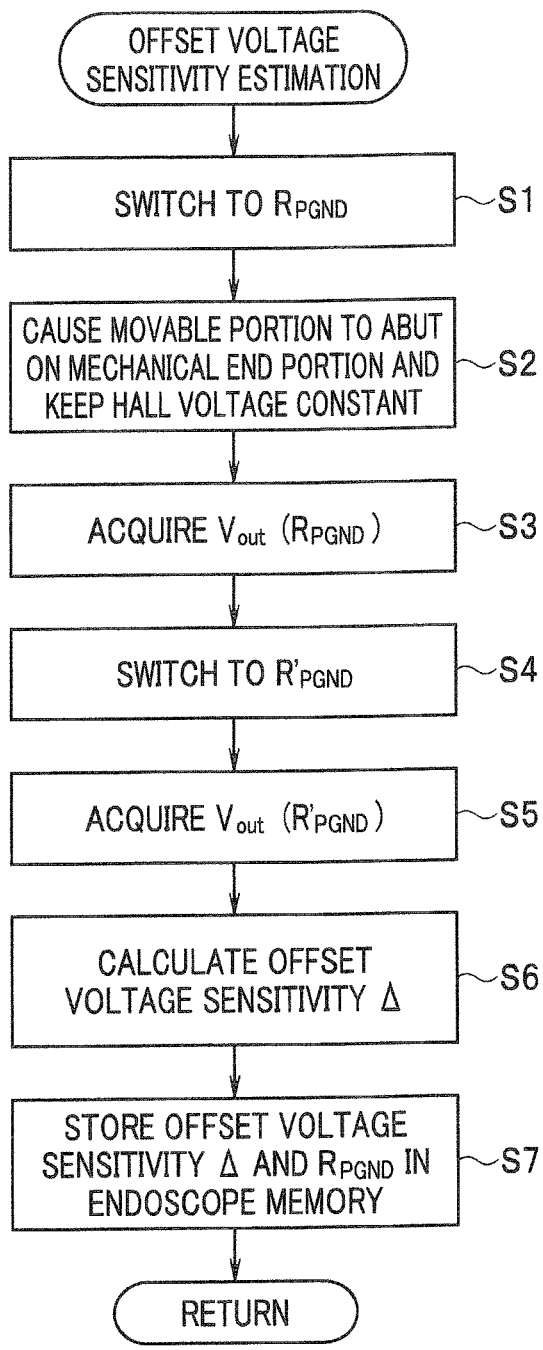
FIG. 5 is a flowchart illustrating a process of offset voltage sensitivity estimation in the endoscope system of embodiment 1 described above.

FIG. 5 is a flowchart illustrating a process of offset voltage sensitivity estimation in the endoscope system. The process illustrated in FIG. 5 is performed in a single calibration apparatus or in the processor 2 including the function of the calibration apparatus by setting the processor 2 at the calibration mode (in this case, an example of being executed in the processor 2 is described).

When a flow enters the process from a main process not illustrated, the resistance switcher 24 switches the wiring of the return signal of the constant current $I_h$ to the wiring of the first wiring resistance value $R_{PGND}$ (step S1).

The drive control section 27 controls the driver circuit 28 to drive the actuator 13, and thereby causes the movable portion including the movable lens 14a to abut on the end (mechanical end portion) of the movable range (step S2).

More specifically, a current is applied to the coil of the actuator 13 from the driver circuit 28, open control of the actuator 13 is performed, and the movable portion is moved until the movable portion abuts on the end of the movable range. Thereby, the movable portion including the movable lens 14a is kept in a constant position, the magnetic flux density that is incident on the Hall element 11A from the magnet 13a is in a state of being kept constant, and the output voltage $V_{out}$ from the Hall element 11A and the differential amplifying circuit 12A basically becomes constant (except for a change amount at a time of the wiring resistance value being changed).

The first output voltage $V_{out}$ ($R_{PGND}$), which is from the differential amplifying circuit 12A and corresponds to the wiring resistance value $R_{PGND}$, is subjected to A/D conversion by the ADC 25. The digitized output voltage $V_{out}$ ($R_{PGND}$) is acquired by the position detection signal correction section 22A, and is temporarily stored in a buffer memory in the position detection signal correction section 22A (step S3).

Next, the resistance switcher 24 switches the wiring of the return signal of the constant current $I_h$ to the second wiring of the second wiring resistance value $R'_{PGND}$ (step S4).

The second output voltage $V_{out}$ ($R'_{PGND}$) which is from the differential amplifying circuit 12A and corresponds to the wiring resistance value $R_{PGND}$ is subjected to A/D conversion by the ADC 25. The digitized output voltage $V_{out}$ ($R'_{PGND}$) is acquired by the position detection signal correction section 22A, and is temporarily stored in the buffer memory in the position detection signal correction section 22A (step S5).

The position detection signal correction section 22A acquires the wiring resistance value $R_{PGND}$ and the wiring resistance value $R'_{PGND}$ from the processor memory 26, and calculates the offset voltage sensitivity Δ as shown in mathematical expression 10 by using the output voltage $V_{out}$ ($R_{PGND}$) and the output voltage $V_{out}$ ($R'_{PGND}$) which are stored in the buffer memory (step S6).

The position detection signal correction section 22A causes the endoscope memory 16 to store the calculated offset voltage sensitivity Δ and the first wiring resistance value $R_{PGND}$ (step S7).

After the processing of step S7 is performed in this way, the flow returns to the main process not illustrated.

Figure 6:
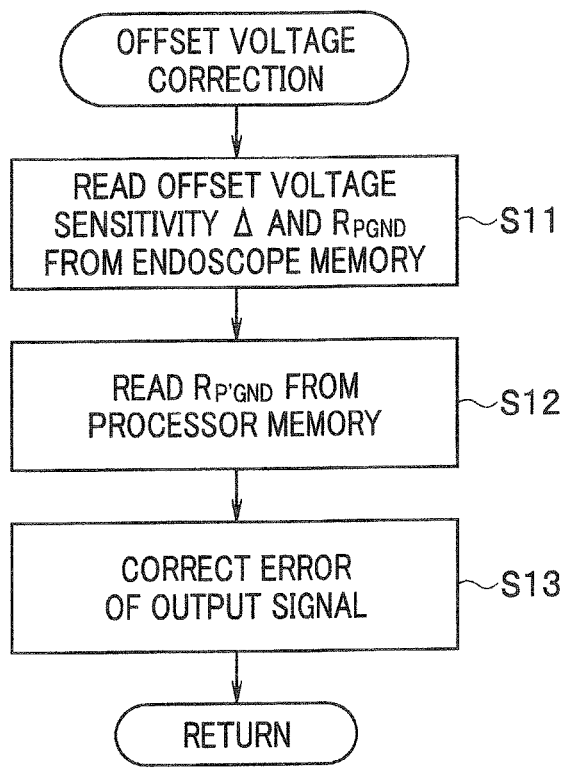
FIG. 6 is a flowchart illustrating a process of offset voltage correction in the endoscope system of embodiment 1 described above.

FIG. 6 is a flowchart illustrating a process of offset voltage correction in the endoscope system. The process illustrated in FIG. 6 is executed every time the position detection signal correction section 22A outputs a position detection signal to the drive control section 27 while the endoscope 1 in which calibration is performed, that is, the endoscope 1 in which the offset voltage sensitivity Δ and the first wiring resistance value $R_{PGND}$ are stored in the endoscope memory 16 is connected to the processor 2 and performs an operation of detecting the position of the movable lens 14a.

When a flow enters the process from the main process not illustrated, the position detection signal correction section 22A reads the offset voltage sensitivity and the first wiring resistance value $R_{PGND}$ from the endoscope memory 16 (step S11).

Further, the position detection signal correction section 22A reads the processor wiring resistance value $R_{PGND}$ from the processor memory 26 (step S12).

The position detection signal correction section 22A calculates the corrected output voltage $V_{correction}$ by using mathematical expression 11 described above based on the offset voltage sensitivity Δ, the first wiring resistance value $R_{PGND}$, the processor wiring resistance value $R_{PGND}$, and the digital output voltage $V_{out}$ which is received from the ADC 25 (step S13).

After the processing in step S13 is performed in this way, the flow returns to the main process not illustrated.

Note that in FIG. 1, the example in which two resistances that are the first wiring resistance $R_{PGND}$ and the second wiring resistance $R'_{PGND}$ are provided in the resistance switcher 24 is described, but three or more resistances having different resistance values may be provided (in other words, at least two resistances differing in resistance value can be provided in the resistance switcher 24). Here, FIG. 7 is a diagram illustrating a modification of the resistance switcher 24.

Figures 7, 8:
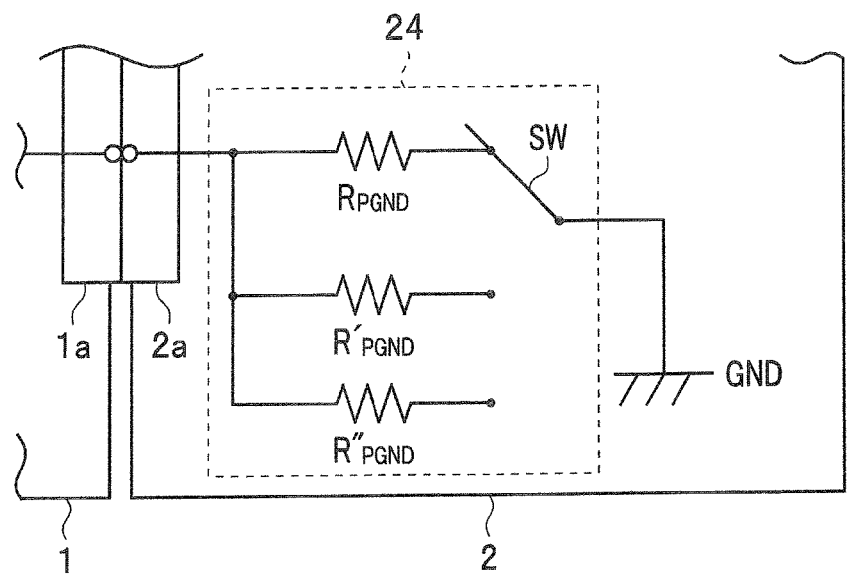
FIG. 7 is a diagram illustrating a modification of a resistance switcher in embodiment 1 described above.
FIG. 8 is a diagram illustrating a modification of storing sets of the offset voltage sensitivity and the wiring resistance value in a processor memory according to model information of the endoscope in embodiment 1 described above.

In an example illustrated in FIG. 7, the first wiring resistance $R_{PGND}$, the second wiring resistance $R'_{PGND}$ which differs in resistance value from the first wiring resistance $R_{PGND}$, and a third wiring resistance $R''_{PGND}$ that differs in resistance value from both of the first wiring resistance $R_{PGND}$ and the second wiring resistance $R_{PGND}$ are provided in the resistance switcher 24 to be switchable by a switch SW.

A first method that uses the resistance switcher 24 of the configuration like this is a method that selects suitable two wiring resistances out of the three wiring resistances, in accordance with the combination of the endoscope 1 and the processor 2. Since the offset voltage sensitivity Δ showing the gradient as shown in FIG. 3 cannot secure precision unless values of the two points which are measured are separate to some degree, two suitable wiring resistances can be selected in accordance with the combination of the endoscope 1 and the processor 2.

More specifically, what is necessary is to obtain the offset voltage sensitivity as described above by using the first wiring resistance $R_{PGND}$ and the second wiring resistance $R'_{PGND}$ for the endoscope 1 of a certain model, to obtain the offset voltage sensitivity Δ as described above by using the first wiring resistance $R_{PGND}$ and the third wiring resistance $R''_{PGND}$ for the endoscope 1 of another model, and the like.

Further, a second method that uses the resistance switcher 24 is a method in which three or more plot points in the graph illustrated in FIG. 3 are obtained by using the three or more wiring resistances, and optimal offset voltage sensitivity Δ is obtained from the three or more plot points.

In general, when the number of resistances differing in resistance value is increased, precision of the offset voltage sensitivity Δ becomes high, so that how many resistances to set in the resistance switcher 24, and how to set the resistance values of the respective resistances can be properly determined in accordance with what precision value is necessary as the offset voltage sensitivity Δ.

Note that it is possible to adopt a configuration using one variable resistance as the resistance switcher 24, but since it is necessary that the resistance value is already known with high precision, a plurality of resistances of fixed resistance values are more preferably provided as illustrated in FIG. 1 and FIG. 7.

In the above description, the endoscope memory 16 is cited as an example as the memory which is caused to store the offset voltage sensitivity Δ and the wiring resistance value $R_{PGND}$ and is readable by the processor 2. However, the memory is not limited to this, but may be the processor memory 26.

FIG. 8 is a diagram illustrating a modification in which sets of the offset voltage sensitivity Δ and the wiring resistance value $R_{PGND}$ are stored in the processor memory 26 in accordance with the model information of the endoscope 1.

A configuration of the endoscope system in the modification is similar to the configuration of the endoscope system illustrated in FIG. 4.

Note that the endoscope memory 16 stores the endoscope model information (model number, serial number and the like), but does not have to store the offset voltage sensitivity Δ and the wiring resistance value $R_{PGND}$.

Further, in the processor memory 26, a plurality of sets of the offset voltage sensitivity Δ and the first wiring resistance value $R_{PGND}$ to the endoscopes 1 of all models which are connectable to the processor 2 are stored for each kind of endoscope model information, as illustrated in FIG. 8.

More specifically, the processor memory 26 stores a set of offset voltage sensitivity Δ1 and a wiring resistance value $R_{P1GND}$ corresponding to a model 1, a set of offset voltage sensitivity Δ2 and a wiring resistance value $R_{P2GND}$ corresponding to a model 2, a set of offset voltage sensitivity Δ3 and a wiring resistance value $R_{P3GND}$ corresponding to a model 3, and so on.

Here, it is assumed that when the models of the endoscopes 1 are the same, the offset voltage sensitivities Δ and the wiring resistance values $R_{PGND}$ are substantially the same even if the endoscopes 1 are individually different, and the offset voltage sensitivity Δ and the wiring resistance value $R_{PGND}$ which are stored in the processor memory 26 are representative values of each model.

However, it is conceivable that even in the endoscopes 1 of the same model, the offset voltage sensitivity Δ and the wiring resistance value $R_{PGND}$ may differ according to production lot, so that information including not only model numbers but also production lots that can be grasped from serial numbers can be used as the endoscope model information.

Furthermore, the processor memory 26 stores the processor wiring resistance value $R_{PGND}$ that is used in position/angle detection of the movable member in the processor 2 itself.

In addition, the processor memory 26 stores information on the actuator 13, the Hall element 11A, the differential amplifying circuit 12A and the like that are known in advance correspondingly to the model number, the serial number and the like of the endoscope 1 as a database.

When the endoscope 1 and the processor 2 are connected, the signal processing circuit 22 reads the endoscope model information from the endoscope memory 16, reads from the processor memory 26 the set of the offset voltage sensitivity Δ and the first wiring resistance value $R_{PGND}$ corresponding to the endoscope model information, corrects an error of the output signal $V_{out}$ by using mathematical expression 11 described above based on a value obtained by multiplying the difference between the first wiring resistance value $R_{PGND}$ and the processor wiring resistance value $R_{PGND}$ by the offset voltage sensitivity Δ, and calculates the output voltage $V_{correction}$.

In the modification, while the information amount that is stored in the endoscope memory 16 decreases, the information amount that is stored in the processor memory 26 increases.

The modification as described with reference to FIG. 8 can be applied in a case where a storage capacity of the endoscope memory 16 cannot be increased, a case where the model of the endoscope 1 which is connectable to the processor 2 is limited, and the like. However, in the case of the processor 2 including the function of the calibration apparatus, calibration is performed to calculate the offset voltage sensitivity Δ when the endoscope 1 of a model that is not recorded in the database is connected, and offset voltage sensitivity Δ and the wiring resistance value $R_{PGND}$ corresponding to new endoscope model information can be added to the database of the processor memory 26.

Note that in the above description, the Hall element 11A is cited as an example as the position/angle sensor 11. However, the position/angle sensor 11 is not limited to the Hall element 11A, but sensors of types that detect differential output by giving a bias current can be widely applied as the position/angle sensor 11. As a specific example of the sensor like this, an MR sensor (magnetoresistive element), an optical type PSD (position sensing device) and the like are cited. Furthermore, the technique of correcting the output voltage $V_{out}$ of the present embodiment may be applied to a pressure sensor using a piezo resistance effect or the like, instead of the position/angle sensor 11.

In the above description, as the memory readable by the processor 2, the endoscope memory 16 and the processor memory 26 are cited as examples. However, the memory is not limited to the endoscope memory 16 and the processor memory 26, but may be a memory readable by the processor 2 via a communication line, for example, a memory or the like of a server in an in-hospital network. In this case, considering that a plurality of types of processors access the server, a database as illustrated in FIG. 8 can be created for each model of the processor 2.

According to embodiment 1 as above, the position detection signal correction section 22A corrects the error of the output voltage $V_{out}$, and outputs a position detection signal based on the corrected output voltage $V_{correction}$, and therefore position detection can be performed with high precision.

The drive control section 27 can perform drive control of the actuator 13 via the driver circuit 28 based on the position detection signal with high precision, and therefore can move the movable member such as the movable lens 14a to a target position with high precision.

As a result, the focus position, the zoom position, the aperture diameter and the like can be set with high precision, image formation performance of the image pickup optical system 14 is enhanced, and a high-resolution endoscope image can be obtained.

Furthermore, the error of the output voltage $V_{out}$ is corrected based on the value obtained by multiplying the difference between the first wiring resistance value $R_{PGND}$ and the processor wiring resistance value $R_{PGND}$ by the offset voltage sensitivity $\Delta$, and therefore high-speed arithmetic operation processing can be easily performed with low load.

In addition, the processor memory 26 is caused to store the processor wiring resistance value $R_{PGND}$ of the wiring for supplying an operation current, and therefore correction of the output voltage $V_{out}$ adapted to the individual processor 2 can be performed regardless of the endoscope 1 of what model is connected.

In this way, even when the arbitrary endoscope 1 and the arbitrary processor 2 are combined, it becomes possible to correct the output voltage $V_{out}$ properly.

Further, when the offset voltage sensitivity $\Delta$ which is necessary to correct the output voltage $V_{out}$ and the first wiring resistance value $R_{PGND}$ are configured to be stored in the endoscope memory 16, it becomes possible to perform optimal correction for each of the individual endoscopes 1.

When the endoscope model information is stored in the endoscope memory 16, a plurality of sets of the offset voltage sensitivities 4 and the first wiring resistance values $R_{PGND}$ are stored in the processor memory 26 according to a plurality of kinds of endoscope model information, the set of the offset voltage sensitivity $\Delta$ and the first wiring resistance value $R_{PGND}$ corresponding to the endoscope model information of the endoscope 1 which is connected to the processor 2 is read from the processor memory 26, and the error of the output voltage $V_{out}$ is corrected, the storage capacity of the endoscope memory 16 can be reduced, and cost of the endoscope 1 can be reduced.

The offset voltage sensitivity $\Delta$ is obtained by switching the first wiring resistance value $R_{PGND}$ and the second wiring resistance value $R_{PGND}$ by the resistance switcher 24 included by the calibration apparatus, and therefore calibration of the endoscope 1 for which calibration is not executed yet can be performed.

If the processor 2 is configured to include the function of the calibration apparatus, the processor 2 can perform calibration properly as necessary when the endoscope 1 is connected to the processor 2 at this time. Thereby, it becomes possible to perform optimal correction of the output voltage $V_{out}$ corresponding to the combination of the processor 2 and the endoscope 1.

Further, when the magnetic flux density which is incident from the magnet 13a which is integrally connected to the movable member is detected by using the Hall element 11A as the position/angle sensor 11, position detection is performed without contact, and therefore movement of the movable member is not hindered.

By using the differential amplifying circuit 12A as the amplifying circuit 12, signal amplification suitable for the output of the Hall element 11A can be performed.

Further, by detecting the magnetic flux density from the magnet 13a of the voice coil motor by the Hall element 11A in the configuration in which the movable member moves by the voice coil motor, the magnet 13a can be used for both drive and detection, which simplifies the configuration and can contribute to reduction in diameter of the endoscope distal end portion.

In this way, according to the endoscope system, the processor, the calibration apparatus, and the endoscope of the present embodiment, the position/angle of the movable member can be detected with high precision even when the power supply path to the position/angle sensor is long and the wiring resistance is unignorable.

Note that the processing of the respective sections described above may be performed by one or more processors which is or are configured as hardware. For example, the respective sections may be respectively processors that are configured as electronic circuits, or may be respective circuit sections in a processor that is configured by an integrated circuit such as FPGA (field programmable gate array). Alternatively, a processor that is configured by one or more CPUs may read and execute a computer program recorded in a recording medium, and thereby execute functions as the respective sections.

Further, in the above description, the endoscope system, the processor, the calibration apparatus, and the endoscope are mainly described, but the present invention may be an operation method for operating the endoscope system, the processor, the calibration apparatus, and the endoscope as described above, or may be a computer program for causing a computer to perform processes similar to the processes of the endoscope system, the processor, the calibration apparatus, and the endoscope, a non-temporary recording medium that records the computer program and is readable by a computer, and the like.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
an endoscope;
a processor to which the endoscope is connectable; and
a memory that is readable by the processor,
wherein:
the endoscope includes:
an image pickup optical system configured to form a subject image;
a movable member configured to adjust an image formation state of the image pickup optical system;
a sensor configured to detect at least one of a position and an angle of the movable member and output a detection signal; and
an amplifying circuit configured to amplify the detection signal and output the detection signal as an output signal,
the memory stores (i) output error sensitivity data, which is based on a ratio of a change amount of an offset voltage included in a voltage of the output signal to a change amount of a wiring resistance value of a wiring for supplying an operation current to the sensor, and (ii) a first wiring resistance value of a wiring for supplying the operation current in a calibration apparatus from which the output error sensitivity data is obtained,
the calibration apparatus comprises one of (i) the processor and (ii) another processor provided separately from the processor,
the processor includes:
a constant current circuit configured to supply the operation current to the sensor;
a signal processing circuit configured to process the output signal from the amplifying circuit; and
a processor memory that stores a processor wiring resistance value of a wiring for supplying the operation current, and the signal processing circuit reads the output error sensitivity data and the first wiring resistance value from the memory when the endoscope and the processor are connected, and corrects an error of the output signal based on a value obtained by multiplying a difference between the first wiring resistance value and the processor wiring resistance value by the output error sensitivity data.

2. The endoscope system according to claim 1, wherein the memory is an endoscope memory included in the endoscope, and the signal processing circuit reads the output error sensitivity data and the first wiring resistance value from the endoscope memory.

3. The endoscope system according to claim 1, wherein:
the endoscope further includes an endoscope memory configured to store endoscope model information,
the memory is the processor memory,
the processor memory stores the processor wiring resistance value, and stores a plurality of sets of the output error sensitivity data and the first wiring resistance value according to a plurality of kinds of endoscope model information, and
the signal processing circuit reads the endoscope model information from the endoscope memory, reads a set of the output error sensitivity data and the first wiring resistance value corresponding to the endoscope model information when the endoscope and the processor are connected, and corrects the error of the output signal based on the value obtained by multiplying the difference between the first wiring resistance value and the processor wiring resistance value by the output error sensitivity data.

4. The endoscope system according to claim 2, wherein:
the calibration apparatus comprises the another processor, and includes:
    a second constant current circuit configured to supply the operation current to the sensor;
    a second signal processing circuit configured to process the output signal from the amplifying circuit;
    a resistance switcher configured to switch between the wiring of the first wiring resistance value for supplying the operation current and a second wiring in the calibration apparatus, the second wiring being a wiring for supplying the operation current and being of a second wiring resistance value different from the first wiring resistance value; and
    a calibration memory configured to store the first wiring resistance value and the second wiring resistance value,
when the endoscope and the calibration apparatus are connected:
    the resistance switcher switches to the wiring of the first wiring resistance value, and the second signal processing circuit acquires a first output signal from the amplifying circuit,
    the resistance switcher switches to the second wiring of the second wiring resistance value, and the second signal processing circuit acquires a second output signal from the amplifying circuit,
    the second signal processing circuit obtains the output error sensitivity data, based on a ratio of a value obtained by subtracting the first output signal from the second output signal to a value obtained by subtracting the first wiring resistance value from the second wiring resistance value, and
    the second signal processing circuit causes the endoscope memory to store the output error sensitivity data and the first wiring resistance value.

5. The endoscope system according to claim 2, wherein:
the calibration apparatus comprises the processor, and further includes:
    a resistance switcher configured to switch between the wiring of the first wiring resistance value for supplying the operation current and a second wiring in the calibration apparatus, the second wiring being a wiring for supplying the operation current and being of a second wiring resistance value different from the first wiring resistance value,
the wiring of the processor wiring resistance value also serves as the wiring of the first wiring resistance value, and
the processor memory stores the first wiring resistance value and the second wiring resistance value.

6. The endoscope system according to claim 1, wherein:
the endoscope further includes a magnet that is integrally connected to the movable member, and
the sensor comprises a Hall element configured to output the detection signal corresponding to a magnetic flux density incident from the magnet.

7. The endoscope system according to claim 6, wherein the amplifying circuit includes a differential amplifying circuit configured to differentially amplify the detection signal that is outputted from the Hall element.

8. The endoscope system according to claim 6, wherein:
the endoscope includes a voice coil motor including a coil and the magnet, and
the movable member is moved integrally with the magnet by the voice coil motor.

9. A processor connectable to an endoscope, the endoscope including (i) a sensor configured to detect at least one of a position and an angle of a movable member and output a detection signal, the movable member being configured to adjust an image formation state of an image pickup optical system, and (ii) an amplifying circuit configured to amplify the detection signal and output the detection signal as an output signal, the processor being configured to read a memory which is configured to store (i) output error sensitivity data, which is based on a ratio of a change amount of an offset voltage included in a voltage of the output signal to a change amount of a wiring resistance value of a wiring for supplying an operation current to the sensor, and (ii) a first wiring resistance value of a wiring for supplying the operation current in a calibration apparatus from which the output error sensitivity data is obtained, the calibration apparatus comprising another processor provided separately from the processor, and the processor comprising:
    a constant current circuit configured to supply the operation current to the sensor;
    a signal processing circuit configured to process the output signal from the amplifying circuit; and
    a processor memory configured to store a processor wiring resistance value of a wiring for supplying the operation current in the processor,
wherein the signal processing circuit reads the output error sensitivity data and the first wiring resistance value from the memory when the endoscope and the processor are connected, and corrects an error of the output signal based on a value obtained by multiplying a difference between the first wiring resistance value and the processor wiring resistance value by the output error sensitivity data.

10. The processor according to claim 9, wherein the memory is an endoscope memory included in the endoscope, and the signal processing circuit reads the output error sensitivity data and the first wiring resistance value from the endoscope memory.

11. The processor according to claim 9, wherein:
the endoscope further includes an endoscope memory configured to store endoscope model information,
the memory is the processor memory,
the processor memory stores the processor wiring resistance value, and stores a plurality of sets of the output error sensitivity data and the first wiring resistance value according to a plurality of kinds of endoscope model information, and
the signal processing circuit reads the endoscope model information from the endoscope memory when the endoscope and the processor are connected, reads a set of the output error sensitivity data and the first wiring resistance value corresponding to the endoscope model information from the processor memory, and corrects the error of the output signal based on the value obtained by multiplying the difference between the first wiring resistance value and the processor wiring resistance value by the output error sensitivity data.

12. The processor according to claim 10, further comprising:
a resistance switcher configured to switch between the wiring of the processor wiring resistance value and a second wiring, the second wiring being a wiring for supplying the operation current and being of a second processor wiring resistance value different from the processor wiring resistance value,
wherein:
the processor memory stores the processor wiring resistance value, and stores the second processor wiring resistance value,
when the endoscope and the processor are connected:
the resistance switcher switches to the wiring of the processor wiring resistance value, and the signal processing circuit acquires a first output signal from the amplifying circuit,
the resistance switcher switches to the second wiring of the second processor wiring resistance value, and the signal processing circuit acquires a second output signal from the amplifying circuit,
the signal processing circuit obtains the output error sensitivity data, based on a ratio of a value obtained by subtracting the first output signal from the second output signal to a value obtained by subtracting the processor wiring resistance value from the second processor wiring resistance value, and
the signal processing circuit causes the endoscope memory to store the output error sensitivity data, and causes the endoscope memory to store the processor wiring resistance value as the first wiring resistance value.

13. A calibration apparatus comprising a processor connectable to an endoscope, the endoscope including (i) a sensor configured to detect at least one of a position and an angle of a movable member and output a detection signal, the movable member being configured to adjust an image formation state of an image pickup optical system, (ii) an amplifying circuit configured to amplify the detection signal and output the detection signal as an output signal, and (iii) an endoscope memory, and the calibration apparatus comprising:
a constant current circuit configured to supply an operation current to the sensor;
a signal processing circuit configured to process the output signal from the amplifying circuit;
a resistance switcher configured to switch between a wiring of a first wiring resistance value for supplying the operation current and a second wiring in the calibration apparatus, the second wiring being a wiring for supplying the operation current and being of a second wiring resistance value different from the first wiring resistance value; and
a calibration memory configured to store the first wiring resistance value and the second wiring resistance value,
wherein when the endoscope and the calibration apparatus are connected:
the resistance switcher switches to the wiring of the first wiring resistance value, and the signal processing circuit acquires a first output signal from the amplifying circuit,
the resistance switcher switches to the second wiring of the second wiring resistance value, and the signal processing circuit acquires a second output signal from the amplifying circuit,
the signal processing circuit obtains output error sensitivity data, based on a ratio of a value obtained by subtracting the first output signal from the second output signal to a value obtained by subtracting the first wiring resistance value from the second wiring resistance value, and
the signal processing circuit causes the endoscope memory to store the output error sensitivity data and the first wiring resistance value.

14. An endoscope connectable to a processor, the endoscope comprising:
an image pickup optical system configured to form a subject image;
a movable member configured to adjust an image formation state of the image pickup optical system;
a sensor configured to detect at least one of a position and an angle of the movable member and output a detection signal;
an amplifying circuit configured to amplify the detection signal and output the detection signal as an output signal; and
an endoscope memory configured to store (i) output error sensitivity data, which is based on a ratio of a change amount of an offset voltage included in a voltage of the output signal to a change amount of a wiring resistance value of a wiring for supplying an operation current to the sensor, and (ii) a first wiring resistance value of a wiring for supplying the operation current in a calibration apparatus from which the output error sensitivity data is obtained,
wherein:
the calibration apparatus comprises one of (i) the processor and (ii) another processor provided separately from the processor, and
when the endoscope and the processor are connected, the output error sensitivity data and the first wiring resistance value are transmitted to the processor from the endoscope memory to cause the processor to correct an error of the output signal.

15. The endoscope according to claim 14, further comprising:
a magnet that is integrally connected to the movable member, wherein the sensor comprises a Hall element configured to output the detection signal corresponding to a magnetic flux density incident from the magnet.

16. The endoscope according to claim 15, wherein the amplifying circuit includes a differential amplifying circuit configured to differentially amplify the detection signal outputted from the Hall element.

17. The endoscope according to claim 15, further comprising:
  a voice coil motor including a coil and the magnet,
  wherein the movable member is moved integrally with the magnet by the voice coil motor.

* * * * *